(12) United States Patent
Mukherjee et al.

(10) Patent No.: US 11,364,482 B2
(45) Date of Patent: Jun. 21, 2022

(54) MIXED METAL OXIDE CATALYST USEFUL FOR PARAFFIN DEHYDROGENATION

(71) Applicant: Exelus, Inc., Fairfield, NJ (US)

(72) Inventors: Mitrajit Mukherjee, Livingston, NJ (US); Vamsi M. Vadhri, North Arlington, NJ (US); Narendra Joshi, Jersey City, NJ (US); Grace Brock, Caldwell, NJ (US)

(73) Assignee: Exelus, Inc., Fairfield, NJ (US)

( * ) Notice: Subject to any disclaimer, the term of this patent is extended or adjusted under 35 U.S.C. 154(b) by 0 days.

(21) Appl. No.: 16/876,957

(22) Filed: May 18, 2020

(65) Prior Publication Data

US 2022/0080390 A1   Mar. 17, 2022

Related U.S. Application Data

(63) Continuation-in-part of application No. PCT/US2019/053710, filed on Sep. 28, 2019, and a
(Continued)

(51) Int. Cl.
*C07C 5/00* (2006.01)
*B01J 23/00* (2006.01)
(Continued)

(52) U.S. Cl.
CPC .............. *B01J 23/002* (2013.01); *B01J 8/02* (2013.01); *B01J 21/063* (2013.01); *B01J 23/06* (2013.01); *B01J 35/023* (2013.01); *B01J 35/08* (2013.01); *B01J 35/1009* (2013.01); *B01J 35/1061* (2013.01); *B01J 35/1066* (2013.01);
(Continued)

(58) Field of Classification Search
CPC ....... C07C 45/34; C07C 5/3332; C07C 11/04; C07C 45/33; C07C 45/35; C07C 47/21; C07C 47/22; C07C 49/205; C07C 51/25; C07C 5/48; C07C 11/02; C07C 49/08; C07C 49/10; C07C 53/08; B01J 2523/48; B01J 23/002; B01J 23/83; B01J 23/847; B01J 23/76; B01J 23/80; B01J 23/8474; B01J 23/8476
See application file for complete search history.

(56) References Cited

U.S. PATENT DOCUMENTS

| | | |
|---|---|---|
| 3,948,808 A | 4/1976 | Box, Jr. et al. |
| 4,144,277 A | 3/1979 | Walker et al. |

(Continued)

OTHER PUBLICATIONS

International Search Report and Written Opinion from International Application No. PCT/US2019/053711 dated Dec. 17, 2019.
(Continued)

*Primary Examiner* — Sharon Pregler
(74) *Attorney, Agent, or Firm* — Frank Rosenberg

(57) ABSTRACT

A catalyst, methods of making, and process of dehydrogenating paraffins utilizing the catalyst. The catalyst includes at least 20 mass % Zn, a catalyst support and a catalyst stabilizer. The catalyst is further characterizable by physical properties such as activity parameter measured under specified conditions. The catalyst may also be disposed on a porous support in an attrition-resistant form and used in a fluidized bed reactor.

21 Claims, 1 Drawing Sheet

Improved Mixed Metal Oxide Catalyst for Paraffin Dehydrogenation

Related U.S. Application Data continuation-in-part of application No. 16/586,980, filed on Sep. 28, 2019, now Pat. No. 11,033,880.

(60) Provisional application No. 62/849,721, filed on May 17, 2019.

(51) Int. Cl.
| | | |
|---|---|---|
| *B01J 37/08* | (2006.01) | |
| *B01J 37/04* | (2006.01) | |
| *B01J 37/06* | (2006.01) | |
| *B01J 37/03* | (2006.01) | |
| *B01J 37/02* | (2006.01) | |
| *B01J 21/06* | (2006.01) | |
| *B01J 8/02* | (2006.01) | |
| *B01J 35/08* | (2006.01) | |
| *B01J 35/10* | (2006.01) | |
| *B01J 35/02* | (2006.01) | |
| *C07C 5/333* | (2006.01) | |
| *B01J 23/06* | (2006.01) | |

(52) U.S. Cl.
CPC ....... *B01J 35/1071* (2013.01); *B01J 35/1076* (2013.01); *B01J 37/0213* (2013.01); *B01J 37/038* (2013.01); *B01J 37/04* (2013.01); *B01J 37/06* (2013.01); *B01J 37/082* (2013.01); *C07C 5/3332* (2013.01); *C07C 2521/06* (2013.01); *C07C 2523/06* (2013.01)

(56) References Cited

U.S. PATENT DOCUMENTS

| | | | |
|---|---|---|---|
| 4,327,238 | A | 4/1982 | Eastman |
| 4,389,337 | A | 6/1983 | Eastman |
| 6,518,476 | B1 | 2/2003 | Culp et al. |
| 6,576,804 | B1 | 6/2003 | Heineke et al. |
| 6,677,497 | B2 * | 1/2004 | Liu .................... C07C 5/3332 585/654 |
| 6,989,346 | B2 | 1/2006 | Heineke et al. |
| 7,087,802 | B2 | 8/2006 | Schindler et al. |
| 8,431,761 | B2 | 4/2013 | Pan et al. |
| 9,713,804 | B2 | 7/2017 | Laha et al. |
| 2013/0165729 | A1 | 6/2013 | Salvanathan et al. |
| 2016/0074838 | A1 | 3/2016 | Hock et al. |
| 2019/0359543 | A1 | 11/2019 | Jantharasuk et al. |
| 2020/0101444 | A1 | 4/2020 | Mukherjee et al. |
| 2020/0101445 | A1 | 4/2020 | Mukherjee et al. |
| 2020/0361838 | A1 | 11/2020 | Mukherjee et al. |

OTHER PUBLICATIONS

International Search Report and Written Opinion from International Application No. PCT/US2019/053710 dated Dec. 17, 2019.
Schweitzer et al., "Propylene Hydrogenation and Propane Dehydrogenation by a Single-Site Zn2+ on Silica Catalyst", ACS Catalysis 2014, 4, 1091-1098.
Sun et al., "Zn—Nb—O catalysts for propylene production via catalytic dehydrogenation of propane", Cat Comm vol. 50, 2014, pp. 73-77.
Harlin et al., "Alumina-Supported Vanadium Oxide in the Dehydrogenation of Butanes", Journal of Catalysis, 2000, vol. 195, p. 67-78.
Volpe et al., "Butane dehydrogenation on vanadium supported catalysts under oxygen free atmosphere", Applied Catalysis A vol. 272, 2004, p. 69-78.
Harlin et al., "Effect of Mg and Zr Modification on the Activity of VOx/Al2O3 Catalysts in the Dehydrogenation of Butanes", Journal of Catalysis, 2001, vol. 203, 242-252.
Harlin et al., "Activity of Molybdenum Oxide Catalyst in the Dehydrogenation of n-Butane", Journal of Catalysis, 1999, vol. 183, 300-313.
Xu et al., "Support effect in dehydrogenation of propane in the presence of CO2 over supported gallium oxide catalysts", Journal of Catalysis, 2006, vol. 239, 470-477.
Liu et al., "Ordered mesoporous carbon catalyst for dehydrogenation of propane to propylene", Chemical Communications, 2011, vol. 47, 8334-8336.
Chen et al., "Study in support effect of In2O3/MOx (M=Al, Si, Zr) catalysts for dehydrogenation of propane in the presence of CO2", Applied Catalysis A, 2011, vol. 407, 20-28.
Stobbe et al., "Potassium promotion of iron oxide dehydrogenation catalysts supported on magnesium oxide: 2. 1-Butene dehydrogenation activity", Journal of Catalysis, 1992, vol. 135, 548-562.
Shimada et al., "Dehydrogenation of isobutane to isobutene with iron-loaded activated carbon catalyst", Applied Catalysis A, 1998, vol. 168, 243-250.
Chen et al., "Dehydrogenation of Isobutane over Zinc Titanate Thin Film Catalysts", Journal of Catalysis, 1996, vol. 161, 730-741.
International Search Report and Written Opinion from International Application No. PCT/US2020/033301 dated Jul. 30, 2020.
International Search Report and Written Opinion from International Application No. PCT/US2020/033441 dated Jul. 30, 2020.

* cited by examiner

*Improved Mixed Metal Oxide Catalyst for Paraffin Dehydrogenation*
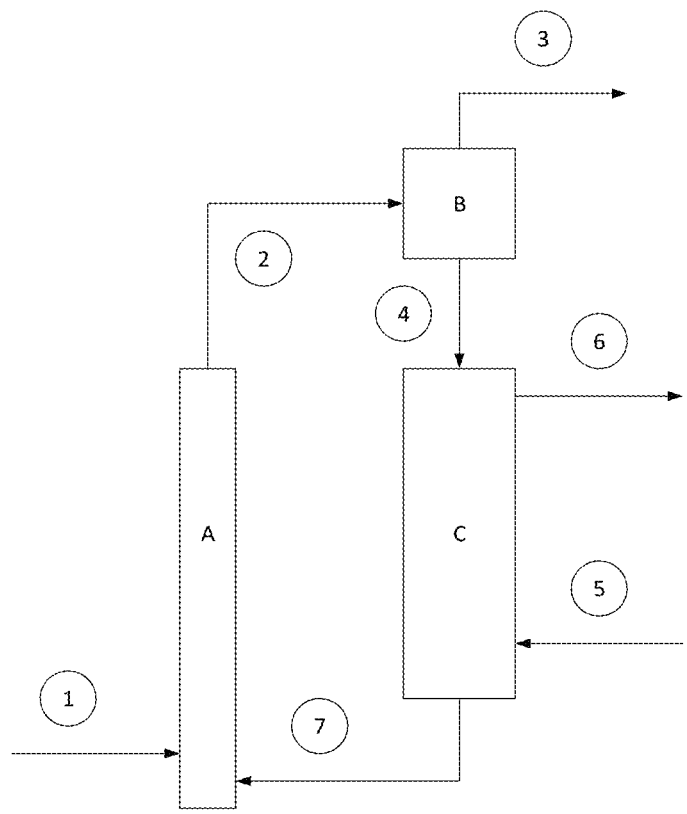

MIXED METAL OXIDE CATALYST USEFUL FOR PARAFFIN DEHYDROGENATION

RELATED APPLICATIONS

This application claims the priority benefit of U.S. Provisional Patent Application Ser. No. 62/849,721 filed May 17, 2019, U.S. patent application Ser. No. 16/586,980 filed Sep. 28, 2019 and PCT application PCT/US19/53710 filed Sep. 28, 2019.

BACKGROUND

The US is currently undergoing a quiet revolution in fossil energy. Recent technological advances, specifically the confluence of horizontal drilling and hydraulic fracturing, have enabled vast gas reserves locked in shale formations to be cost effectively tapped for the first time. An estimated 2 quadrillion cubic feet of natural gas is held in these unconventional reserves in the US, enough to supply the nation's needs for many decades.

The ability to access these resources has led to a sudden decoupling of the traditional link between petroleum and natural gas prices. Domestic natural gas prices have fallen to historically low levels as a result of the introduction of 4.5 trillion cubic feet per year of shale gas, accounting for 20% of the nation's total gas supply.

The abundance of cheap propane, ethane, and methane from shale gas and stranded gas will facilitate cost-competitive paths in the production commodity chemicals such as light olefins. In particular, the on-purpose production of propylene has grown as more steam crackers shift from naphtha feed to lighter shale condensates. This is especially true in the United States, where shale gas exploitation has grown exponentially, amplifying the issue of supply due to the strong growth in propylene demand compared with that of ethylene. Steam cracker units cannot fill this gap due to the low propylene/ethylene ratio. In this respect, other production routes could be profiled as an interesting alternative to overcome this issue.

The shift from naphtha toward light feeds that are derived from tight oil, for the production of ethylene in steam crackers, has impacted the global propylene and crude $C_4$ production capacity. Therefore, routes for the on-purpose production of light olefins have received considerable interest. Catalytic dehydrogenation provides the possibility of high selectivity to a single olefin product—much higher than can be expected from steam crackers alone. The amount of propylene produced by dehydrogenation was 5 million tons in 2017 and is expected to increase.

Two patented industrial processes for the dehydrogenation of alkanes are currently in commercial use—namely, the Oleflex process which uses a Platinum based catalyst and the Catofin process which uses a Chromium based catalyst. Platinum is expensive and currently sells for $27,000/kg making platinum-based dehydrogenation processes very expensive. Chromium-based catalysts are comparatively cheaper. However, chromium is a known carcinogen. The object of the present invention is to provide an improved mixed-metal oxide catalyst for the dehydrogenation of paraffins which is preferably essentially free of either Platinum or Chromium.

PRIOR ART

Compared to metallic platinum and chromium oxide, zinc oxide (ZnO) is an inexpensive and low-toxic alternative for dehydrogenation of propane. Zinc has been shown to activate propane through dissociative adsorption over zinc oxide species. For instance, U.S. Pat. No. 2,279,198 describes an active, stable and regenerable catalytic system consisting of zinc oxide along with other metal oxides and promoters for the dehydrogenation of alkanes and other organic compounds. Isobutane conversion as high as 26.4% has been reported at 510° C. Successively precipitated ZnO over zirconium oxide was shown to be active and stable for the dehydrogenation reaction while addition of small amounts of $Li_2O$ and CaO were shown to further improve the catalyst activity and stability.

Numerous other Zn-based catalysts have been explored for dehydrogenation of hydrocarbons. For example, it is reported that when Zn is introduced into acidic zeolites like H-ZSMS, the reaction rate for dehydrogenation of paraffins increases[2-13]. The $Zn^{2+}$ species are reported to reside in the cation exchange sites of the zeolite and have a tetrahedral orientation. The main products are aromatic compounds and the selectivity to olefins is usually low (<40%). While the role of Zn in these reactions is greatly debated, it is believed that Zn carries out the two-fold function of promoting the dehydrogenation of the hydrocarbon as well as depleting the surface hydrogen pool by the catalytic recombinative desorption of H-atoms and $H_2$[14].

Zinc has also been used as a promoter for alkane dehydrogenation catalysts[15-20]. For example, studies in literature have shown that the addition of Zn to Pt or Cr containing catalysts resulted in increasing the alkene selectivity during alkane dehydrogenation. It is believed that zinc modifies the geometric and electronic properties of the metallic phase of Pt and studies showed that the addition of zinc to Pt—$Al_2O_3$, PtSn—$Al_2O_3$,[15] and PtSn—$MgAl_2O_4$ formulations significantly improved their overall performance for propane dehydrogenation[17]. Zinc is known to alloy with platinum and the formation of the alloy is believed to increase the electronic density on the metallic Pt which weakens the alkene adsorption[15] resulting in reduced coke formation and lower associated by-product gases such as methane and ethane.

Zinc was also shown to be effective in increasing the activity of hematite towards ethylbenzene dehydrogenation[21]. The authors claimed that while zinc oxide by itself was inactive for the reaction, it increased the activity of hematite towards the dehydrogenation by stabilizing the $Fe^{3+}$ species.

Zinc based catalysts have been shown to be active in the oxidative dehydrogenation of hydrocarbons. While it was known that simple iron oxide, $\alpha$-$Fe_2O_3$ catalyzes a rather selective production of butadiene via the oxidative dehydrogenation of butenes and in some cases n-butane, Rennard and Kehl showed that addition of zinc oxide to iron oxide leads to the formation of $ZnFe_2O_4$ which further increases the selectivity to butadiene under identical conditions[22]. For example, the selectivities for butadiene on $Fe_2O_3$ were 83% at 325° C. and 43% at 375° C., while on $ZnFe_2O_4$ they were 89% at 325° C. and 88% at 375° C. Comparison of these results with those on iron oxide suggests that zinc ferrite is a more selective oxidation catalyst because it has a higher density of selective oxidation sites and a lower density of combustion sites, and because its combustion sites are less active than those on iron oxide[22-24]. Numerous methods of synthesis with and without the presence of promoters have been described in literature (U.S. Pat. Nos. 3,743,683, 3,951,869). For example, it is reported that when a zinc ferrite catalyst doped with chromium or aluminum was used, catalytic activity towards dehydrogenation was increased[25].

Zinc has been used as a support for the dehydrogenation of lower alkanes. Zinc aluminate has been used as a catalyst support due to its low specific surface area and high hydrothermal stability[26-28]. U.S. Pat. Nos. 5,344,805; 5,430,220; and EP 0557982A2 describe a process for dehydrogenating at least one alkane comprising 2 to 8 carbon atoms to an alkene in the presence of steam and a catalyst composition comprising zinc aluminate and platinum. The addition of zinc oxide to alumina for a Pt based catalyst was shown to increase the rate of dehydrogenation as well as the selectivity of alkene as a result of the suppression of the decomposition reaction and coke formation[29]. However, zinc aluminates by themselves are inactive as dehydrogenation catalysts. They require an additional metal like platinum as part of the catalyst composition to be effective.

Pt and Cr free catalysts have been synthesized via a coprecipitation method using nitrates of various metals and were shown to be active and selective for the dehydrogenation of isobutane to isobutene (U.S. Pat. No. 9,713,804B2, WO2013091822A1). The most active, selective and stable composition consisted of mixed Zn, Mn and Al oxides. Numerous promoters, selected from alkali metals (K, Cs), non-metals (Si) and transition metals (Fe, Cr, Cu, Zr, Ce, etc.) were used to promote these catalysts with varying degrees of success. These catalysts showed high activity (up to 56% conversion of isobutane) and high selectivity (up to 96%) to isobutene at 550° C. and a space velocity of 0.6 $hr^{-1}$. These catalysts also showed reasonable stability with just a moderate drop in activity for up to 500 reaction-regeneration cycles. However, no data was provided for the application of this catalyst to other hydrocarbons like ethane and propane. Zinc titanate is reported to be active in the dehydrogenation of alkanes. Zinc titanate was first reported to be active for the dehydrogenation of isobutane by Phillips Petroleum resulting in a modest isobutene yield. Later, it was also applied for the dehydrogenation of a number of paraffins, olefins, cycloaliphatics and alkyl aromatic compounds having from 2 to 12 carbon atoms per molecule as described in U.S. Pat. Nos. 4,368,344A, 4,389,337A, 4,524, 144A, 4,144,277A, 4,394,297A, 4,218,346A.

U.S. Pat. Nos. 4,228,040A, 4,389,337, 4,463,213, 4,176, 140 and 4,327,238 show that various promoters, either transition metals, alkali metals or alkaline earth metals can be used with the zinc titanate of U.S. Pat. No. 4,144,277 to improve the yield of unsaturated compounds.

The catalyst was usually prepared by intimately mixing suitable proportions of zinc oxide and titanium dioxide wherein the atomic ratio of zinc to titanium was usually close to 2:1 and calcining the resulting mixture in air at a temperature in the range of 675° to 975° C. In 4,463,213, for example, a slurry of powdered zinc titanate was combined with alumina and nitric acid to form a hydrosol that was treated with ammonium hydroxide (aqueous ammonia) to produce a hydrogel.

High yields of the unsaturated compounds were reported. Ethylene yield of 33% from ethane at 666° C. (U.S. Pat. No. 4,389,337), propylene yield of 67.75% at 621° C. (U.S. Pat. No. 4,228,040) and isobutene yield of 54% at 625° C. (U.S. Pat. No. 4,463,213) are reported to list a few. Usually, the reaction time was 3 minutes followed by a nitrogen purge for 3 minutes and then regeneration in air for 6 minutes. It is mentioned that the catalysts are subjected to numerous reaction-regeneration cycles. However, since no stability data is presented it is not clear whether the catalyst performance changes over the course of time with successive reaction-regeneration cycles. It should also be noted that the dehydrogenation tests were carried out in the presence of nitrogen as a diluent.

Lysova et al. studied the effect of the chemical composition of the $ZnO$—$TiO_2$ catalytic system on its phase composition and catalytic properties in the oxidative and non-oxidative dehydrogenation of isobutane[30]. It was found that samples with an atomic ratio of zinc to titanium ≥2 exhibited the highest selectivity with high specific activity. It was reported that $ZnO$—$TiO_2$ system was active and selective in ODH of isobutane at 570° C., the maximum yield of isobutene being 54%.

Chen et al. prepared thin films (80-100 nm) of zinc titanate with Zn/Ti ratios between 0.5 and 2.7 on 200 Si(100) wafers via the metalorganic decomposition (MOD) technique and investigated them for alkane dehydrogenation reactions[31]. Catalytic testing of these films for isobutane dehydrogenation showed a clear correlation between the structure and the catalytic performance which depended on the film stoichiometry. Zinc titanate phases, with a Zn/Ti ratio close to 2, had a cubic crystal structure and were found to be active for dehydrogenation while the other phases were not. The isobutane conversion was 2% at 823 K and 8 mol % at 923 K, with a selectivity of 90% to isobutene.

Schweitzer et al. tested a $Zn/SiO_2$ catalyst for the dehydrogenation of propane[32]. The reaction was run under differential conditions (target conversion of less than 10%). Propylene selectivity was reported to be >95% at 550 C and the catalyst lost only 50% of its activity in 12 hours. In this catalyst, the $Zn^{2+}$ center is coordinated with three O centers of the $SiO_2$ surface and is believed to be the active species. It was shown through various computational and characterization methods that the active site catalyzes the heterolytic cleavage of the C—H bonds of propane and the undesired C—C cleavage reactions are shown to be kinetically less favorable resulting in a higher propylene selectivity. However, the dehydrogenation reaction was run with an extremely dilute 3% propane in Argon reaction mixture. Additionally, while it was mentioned that conversion reached 20% at 550° C., no time on stream data is provided for high conversions.

Sun et al. report that Zn—Nb—O oxides are active and selective in the catalytic dehydrogenation of propane to propylene[33]. A propylene yield of 28.1 wt. % with selectivity of 84% were observed over the catalyst which was calcined at 600° C. and had a molar ratio of $ZnO/Nb_2O_5$=3. $ZnNb_2O_6$ was suggested to be the active site for the dehydrogenation reaction. Temporary, reversible deactivation was observed which was attributed to the formation of coke while the loss of ZnO species leading to the formation of $Zn_3Nb_2O_8$ phase was suggested to be the reason for the irreversible deactivation of the catalyst.

U.S. Pat. No. 7,087,802, US Published Patent Application No. 2016/0074838 and U.S. Pat. No. 6,518,476 describe catalyst systems for the oxidative and/or non-oxidative dehydrogenation of light alkanes where the catalyst consists of a support and an active component. The support is generally a heat-resistant oxide and could be selected from zirconium dioxide, zinc oxide, aluminum oxide, silicon dioxide, titanium dioxide, magnesium oxide, lanthanum oxide, cerium oxide and mixtures thereof. The active component could be a precious metal like Pt or Pd or can be from the other transition, alkali or alkaline earth metal or a mixture of the above components. It was also suggested that the dehydrogenation catalyst described in these patents can be used in the form of a fixed bed in the reactor or in the form of a fluidized bed with an appropriate shape.

Despite these and other efforts, there remains a need in the industry to develop cost-effective, environmentally friendly dehydrogenation catalysts that are commercially viable.

FOOTNOTED CITATIONS

2. Mole, T., Anderson, J. R., and Creer, G., Appl. Catal. 17, 141 (1985).
3. Shibata, M., Kitagawa, H., Sendoda, Y., and Ono, Y., in "Proceedings of 7th International Zeolite Conference," p. 717. Elsevier, Tokyo, 1986.
4. Scurrell, M. S., Appl. Catal. 41, 89 (1988).
5. Ono, Y., and Kanae, K., J. Chem. Soc.-Faraday Trans. 87, 669 (1991).
6. Roessner, F., Hagen, A., Mroczek, U., Karge, H. G., and Steinberg, K. H., in "Proceedings of the 10th International Congress on Catalysis" (L. Guczi, F. Solymosi, and P. Tetenyi, Eds.), p. 1707. Elsevier, Budapest, 1992.
7. Iglesia, E., and Baumgartner, J. E., in "Abstracts 206th American Chemical Society Meeting," Chicago, Ill., 1993, p. 746.
8. Dufresne, L. A., and le van Mao, R., Catal. Lett. 25, 371 (1994). 31. Hagen, A., Roessner, F., and Reschetilowski, W., Chem. Eng. Technol. 18, 414 (1995).
9. Biscardi, J. A., and Iglesia, E., Catal. Today 31, 207 (1996).
10. Berndt, H., Lietz, G., Lucke, B., and Volter, J., Appl. Catal. 146, 351 (1996).
11. Berndt, H., Lietz, G., and Volter, J., Appl. Catal. 146, 365 (1996).
12. Kwak, B. S., and Sachtler, W. M. H., Korean J. Chem. Eng. 13, 356 (1996).
13. Viswanadham, N., Pradhan, A. R., Ray, N., Vishnoi, S. C., Shanker, U., and Prasada Rao, T. S. R., Appl. Catal. 137, 225 (1996).
14. Joseph A. Biscardi, Enrique Iglesia, Journal of Catalysis, (1999) 182, 117-128.
15. Yu C L, Xu H Y, Ge Q J, Li W Z. J Mol. Catal A Chem. 2007; 266(1-2):80-87.
16. Zhang Y W, Zhou Y W, Shi J J, Sheng X L, Duan Y Z, Zhou S J, Zhang Z W. Fuel Process Technol. 2012; 96:220-227.
17. Wang Y J, Wang Y M, Wang S R, Guo X Z, Zhang S M, Huang W P, Wu S H. Catal Lett. 2009; 132(3-4):472-479.
18. Silvestre-Albero J, Serrano-Ruiz J C, Sepulveda-Escribano A, Rodriguez-Reinoso F. Appl Catal A Gen. 2005; 292:244-251.
19. Bosch P, Valenzuela M A, Zapata B, Acosta D, Aguilarrios G, Maldonado C, Schifter I. J Mol Catal. 1994; 93(1):67-78.
20. Yu, Z.; Sawada, J. A.; An, W.; Kuznicki, S. M. AlChE J. 2015, 61, 4367-4376.
21. Hugo Ernane Leite Bomfim, Alcineia Conceição Oliveira and Maria do Carmo Rangel; React. Kinet. Catal. Lett. (2003), 80, 2, 359.
22. Rennard, R.; Kehl, W. J. Catal. (1971), 21, 282.
23. H. Kung,* B. Kundalkar, M. C. Kung, and W. H. Cheng J. Phys. Chem., (1980) Vol. 84, No. 4, 382-388
24. F.-Y. Qiu, L.-T. Weng, E. Sham, P. Ruiz, B. Delmon, (1989) Appl. Catal., 51, 235.
25. J. A. Toledo, P. Bosch, M. A. Valenzuela, A. Montoya, N. Nava; (1997) J. Mol. Catal. A, 125, 3.
26. A. Kiennemann, H. Idriss, J. P. Hindermann, J. C. Lavalley, A. Vallet, P. Chaumette and P. Courty, Appl. Catal. 59 (1990) 165.
27. G. P. Chernyuk, L. I. Chelyadin and Y. S. Mazurenko, Neftekhimiya 16 (1976) 683.
28. M. E. Olbrich and J. H. Kolts, AlCHE Spring Nat. Meet., New Orleans, Apr. 6-10, 1986.
29. Hideki SATOH, Hiroyuki TAGUCHI, Hiroshi MIURA; J. Japan Petroleum Institute, 1995, 38, 1, 34-39.
30. N. N. Lysova, D. N. Tmenov and P. Luk'yanenko, Russ. Zh. Prikl. Khim., 65 (1992), 1848; J. Appl. Chem. (1993) 1500 (Engl. translation).
31. Z. X. Chen, A. Derking, W. Koot, and M. P. van Dijk; JOURNAL OF CATALYSIS (1996) 161, 730-741.
32. Neil M. Schweitzer, Bo Hu, Ujjal Das, Hacksung Kim, Jeffrey Greeley, Larry A. Curtiss, Peter C. Stair, Jeffrey T. Miller, and Adam S. Hock; ACS Catal. (2014), 4, 1091-1098.
33. Ya-nan Sun, Chuancheng Gao, Lei Tao, Guowei Wang, Dongmin Han, Chunyi Li, Honghong Shan; Catalysis Communications; 50 (2014) 73-77.

SUMMARY OF THE INVENTION

In a first aspect, the invention provides a mixed-metal oxide catalyst suitable for the dehydrogenation of paraffins having 2-8 carbon atoms comprising oxides of zinc (Zn) as the active catalytic species wherein Zn makes up at least 20 wt % of the total weight of the catalyst, oxides of aluminum (Al), silicon (Si), and titanium (Ti), or mixtures thereof as the catalyst support wherein the catalyst support makes up 10 to 75 wt % of the total weight of the catalyst, preferably 20 to 70 wt % and oxides of metals as catalyst stabilizers selected from the group of cerium (Ce), dysprosium (Dy), erbium (Er), europium (Eu), gadolinium (Gd), lanthanum (La), neodymium (Nd), praseodymium (Pr), samarium (Sm), terbium (Tb), ytterbium (Yb), yttrium (Y), tungsten (W) and zirconium (Zr) and combinations thereof wherein the catalyst stabilizer makes up 0.1 to 20 wt % of the total weight of the catalyst, preferably 1 to 10 wt % and characterizable by
  a) Activity Parameter >90,000,
  b) Selectivity Parameter <0.5 and
  c) Stability parameter <0.005
using a test where the metal oxide catalyst is loaded in a fixed-bed reactor such that the $50>d_T/d_P>10$ (diameter of tube to diameter of catalyst particles) and $200>L/d_P>50$ (length of catalyst bed to diameter of catalyst particles) and $2>d_P>0.5$ mm exposed to a feed stream comprising of propane at a temperature of 650° C., atmospheric pressure and a feed rate of 10 $hr^{-1}$ weight hourly space velocity. The catalyst support (CS) plus stabilizer (ST) is also called a stabilized catalyst support.

In some preferred embodiments, the catalyst can be further characterized by one or any combination of the following features: an activity parameter of at least 95,000 or an activity in the range of 90,000 to 125,000; wherein the catalyst comprises at least 30 wt % or 20 to 70 or 25 to 70 or 30 to 70 or no more than 60 or no more than 50 wt % of the catalyst; or wherein the catalyst support comprises 20 to 70 or 25 to 70 or 30 to 70 or no more than 60 or no more than 50 wt % of the catalyst; wherein the support stabilizer comprises 0.1 to 20 or 0.2 to 15 or 0.3 to 10 wt % of the catalyst; less than 0.5 wt % S, less than 0.5 wt % of S, N and halides, preferably less than 0.2 wt % 5; a Brunauer-Emmet-Teller (BET) surface area of at least 5 or at least 10 m²/g; wherein the number average particle diameter of the mixed-metal oxide catalyst is in the range of 30-3000 microns (μm).

Since the catalyst cannot be completely distinguished from the prior art based solely on its elemental composition, the measurement described above is needed for a unique characterization of the catalyst. In various embodiments, the catalyst may be further characterized by any of the compositions or physical characteristics described herein.

In another aspect, the invention provides a method for preparing a catalyst comprising the steps of: a) dissolving salts of active material, catalyst support and support stabilizer in a solvent; b) coprecipitating the salts using a precipitating agent; c) washing the precipitate, preferably with an aqueous solution; and d) drying and calcining the resultant precipitate to produce the mixed metal oxide catalyst. Preferably, the wash solution comprises ammonium hydroxide (aqueous ammonia) to remove sulfate, nitrate, and/or chloride. For purposes of the present invention, the salts are anions, preferably sulfate, nitrate, or chloride. The solubility of various chemical compounds in selected solvents is known or can be determined by routine experimentation. Preferred salts are nitrates and sulfates. Preferably, the solvent comprises aqueous ammonia. Preferably, the precipitating agent comprises aqueous ammonia.

In another aspect, the invention provides a method for preparing a catalyst comprising the steps of:
 a) providing a salt solution comprising salts of active catalyst, catalyst support, and support stabilizer dissolved in a solvent;
 b) impregnating porous spheres with the salt solution;
 c) drying and calcining the porous spheres to produce the mixed metal oxide catalyst. Preferably, the porous spheres are washed with an aqueous solution. Preferably, the volume average pore diameter of the porous bead is in the range of 3 to 3000 nm. In some embodiments, the volume average pore diameter of the mesoporous bead is in the range of 3-500 nm or 3-25 nm.

In another aspect, the invention provides a method for preparing a catalyst comprising the steps of: a) mixing oxides of active catalyst, catalyst support, and support stabilizer in a solvent; b) spray drying and calcining the oxides to produce the mixed metal oxide catalyst suitable for use in a fluidized bed reactor.

In another aspect, the invention provides a method for preparing a catalyst comprising the steps of: a) mixing oxides of active catalyst, catalyst support, and support stabilizer in a solvent; b) drying and calcining the oxides to produce the mixed metal oxide catalyst suitable for use in a fixed bed reactor.

Binders can be added to the mixed-metal oxide catalysts to provide sufficient mechanical strength for use in commercial reactors.

In some preferred embodiments, oxides of zinc, oxides of catalyst support and oxides of a catalyst stabilizer are combined with an hydrated alumina (such as boehmite alumina powders sold under the tradename Dispal®) that is modified with one or more alkaline earth elements (typically Ca and/or Mg) which moderate Lewis acid sites. In some embodiments, a slurry comprising oxides of zinc, titanium and zirconium are combined with an alkaline earth-modified hydrated alumina. The amounts of each component are selected so that the final catalyst composition comprises at least 20 mass % Zn and preferably the final catalyst comprises comprises 20 to 70 or 25 to 70 or 30 to 70 catalyst support (CS) and the support stabilizer (ST) comprises 0.1 to 20 or 0.2 to 15 or 0.3 to 10 wt % of the final catalyst.

The catalyst support or the mixed metal oxide catalyst can, in some embodiments, be calcined at 500-1,100° C., preferably at 600-900° C. and most preferably at 700-850° C. for 2-6 hrs in an oxygen containing atmosphere, preferably air.

The invention also includes processes of dehydrogenating a paraffin (preferably propane or isobutane), comprising contacting the paraffin with any of catalysts described herein in a reaction chamber under conditions sufficient to dehydrogenate the paraffin and resulting in an olefin. The sufficient conditions are conventional conditions for dehydrogenation or identified with no more than routine experimentation.

In a further aspect, the invention provides a process for continuous dehydrogenation of paraffins having 2-8 carbon atoms, preferably propane or isobutane, comprising:
 contacting said paraffins with the catalyst composition according to any one of claims 1-12 at a reaction temperature of 500-800° C., a space velocity of 0.1-25 $hr^{-1}$ or 0.1-15 $hr^{-1}$ and a pressure of 0.01-0.2 MPa for a reaction period in the range of 0.05 seconds to 10 minutes, and
 regenerating the said catalyst with an oxygen-containing gas wherein said catalyst regeneration is performed at a reaction temperature of 500-800° C., a pressure of 0.01-0.2 MPa and a regeneration period ranging from 0.05 seconds to 10 minutes.

In some preferred embodiments, the contacting step is carried out in a fluidized bed reactor or a fixed-bed swing reactor.

Another aspect of the invention provides a continuous method for dehydrogenating paraffins having 2-8 carbon atoms wherein the process is performed at a reaction temperature of 500-800° C., a space velocity of 0.1-25 $h^{-1}$ (or, in some embodiments, 0.1 to 1 $h^{-1}$) and a pressure of 0.01-0.2 MPa. The fluidized bed version of the method is shown in FIG. 1. In this method, the paraffin feedstock 1 is contacted with the catalyst under dehydrogenation conditions for a reaction period in the range of about 0.05 second to 10 minutes in Reactor/Riser A. Following the reaction period, the Reactor outlet stream 2 containing catalyst and product gas flows to the Cyclone/Disengager B in which the catalyst is separated from the Product Stream 3. The Separated Catalyst stream 4 is thereafter regenerated in Regenerator C by contacting said catalyst with Combustion Air 5. The catalyst regeneration is performed at a temperature of 500-800° C., a pressure of 0.01-0.2 MPa and a regeneration period ranging from about 0.05 seconds to 10 minutes and producing Flue Gas stream 6 and Regenerated Catalyst stream 7, which is routed again to the Reactor/Riser A. The process can be carried out using a Reactor/Riser A configured as a fluidized bed reactor or as a fixed-bed swing reactor.

In some preferred embodiments, the invention provides advantages such as: the product of the catalyst activity and catalyst selectivity exceeding 0.1 ton of product per hour per ton of catalyst; and the overall catalyst consumption does not exceed 1 kg of catalyst per ton of product. None of the prior art catalysts (substantially without Pt or Cr) listed in the prior art meet these two characteristics simultaneously.

The invention is further elucidated in the examples below. In some preferred embodiments, the invention may be further characterized by any selected descriptions from the examples, for example, within ±20% (or within ±10%) of any of the values in any of the examples, tables or figures; however, the scope of the present invention, in its broader aspects, is not intended to be limited by these examples.

BRIEF DESCRIPTION OF THE DRAWING

FIG. 1 shows illustrates a reaction scheme for a dehydrogenation. Paraffins 1 enter reactor A. The products 2 pass into separator B wherein olefins 3 are separated and catalyst 4 is regenerated in Regenerator C and regenerated catalyst 7 is returned to the reactor. Oxygen-containing gas 5 passes into the Regenerator and stream 6 exits the Regenerator.

GLOSSARY

Arrhenius Activation Energy (E): The Arrhenius equation gives the quantitative basis of the relationship between the activation energy and the rate at which a reaction proceeds. Arrhenius activation energy term from the Arrhenius equation is as an experimentally determined parameter that indicates the sensitivity of the reaction rate to temperature. From the equation, the activation energy can be found through the relation $$k=k_0 e^{-E/RT}$$

Where k is the rate constant (units 1/sec) of a reaction at temperature T, $k_0$ is pre-exponential factor, E is activation energy for the reaction, R the universal gas constant, T the reaction temperature (in Kelvin). k is calculated from conversion (x) and residence time ($\tau$)(measured in seconds) as follows $$k=-\ln(1-x)/\tau$$

Activity Parameter—The catalyst activity is quantified by the activity parameter which is the pre-exponential factor in the Arrhenius equation $k_0$ for the dehydrogenation reaction, an empirical relationship between temperature and rate coefficient using a value of 81.7 kJ/mole for E the Activation Energy for the dehydrogenation reaction using for Titania based catalyst.

Selectivity Parameter—Since selectivity of propylene varies with propane conversion, a method is required to compare selectivity obtained by different catalysts under various conversions. Selectivity parameter is calculated from the ratio of the first-order rate constant of the propylene cracking reaction ($k_C$) to the first-order rate constant of the propane dehydrogenation reaction ($k_D$) and remains constant irrespective of the propane conversion. A catalyst producing propylene with a high selectivity will have a selectivity parameter <0.2.

The selectivity parameter (=$k_C/k_D$) is calculated from propane conversion (x) and propylene yield (y) by solving the equations shown below:

$$k_D=-\ln(1-x)/\tau$$

$$y=[k_D/(k_C-k_D)][e^{(-kD\tau)}-e^{(kC\tau)}]$$

Stability Parameter—The loss of catalyst activity with time is quantified by the stability parameter which measures the rate of change of catalyst activity with time. A catalyst with high stability will have a low stability parameter value <0.005.

$$\text{Stability Parameter}=(k_{D0}-k_{Dt})/t$$

Where $k_{Dt}$ is the rate constant of dehydrogenation of propane at time t, $k_{D0}$ is the rate constant of dehydrogenation of propane at time 0 and t is the time on stream (in hours) For instance, at a reaction temperature of T=625° C. (898 K) and residence time $\tau$=1 second, for a propane conversion of x=46% and propylene yield of y=42%

Activity Parameter=35,028
Selectivity Parameter=0.23

Characterization of the catalyst is conducted in the absence of a diluent gas such as nitrogen, hydrogen, steam or helium.

Attrition Index: The attrition resistance of catalysts used in fluidized reactor systems are characterized by the Attrition Index determined by ASTM tests such as AJI-Air Jet Index which is the percent attrition loss at 5 hours (ASTM D5757-Standard Test Method for Determination of Attrition of FCC Catalysts by Air Jets).

Calcination Temperature—The term "calcination temperature" refers to the maximum temperature utilized as an intermediate step in the catalyst synthesis procedure intended to convert the metal salts to their oxide form.

Conversion—The term "conversion of a reactant" refers to the reactant mole or mass change between a material flowing into a reactor and a material flowing out of the reactor divided by the moles or mass of reactant in the material flowing into the reactor. For propane dehydrogenation, conversion is the mass of propane reacted divided by the mass of propane fed.

Geldart Classification: Catalyst particles can be characterized by four so-called "Geldart Groups". The groups are defined by their locations on a diagram of solid-fluid density difference and particle size. For Group A the particle size is between 20 and 100 μm, and the particle density is typically less than 1.4 g/cm$^3$. For Group B, the particle size lies between 40 and 500 μm and the particle density between 1.4-4 g/cm$^3$. Most particles used in fluidized beds are Geldart Group A powders. In some embodiments, catalysts of the present invention have the characteristics of Group A; in some embodiments, catalysts of the present invention have the characteristics of Group B.

"Particle size" is number-average particle size, and, for non-spherical particles, is based on the largest dimension.

Pore size—Pore size relates to the size of a molecule or atom that can penetrate into the pores of a material. As used herein, the term "pore size" for zeolites and similar catalyst compositions refers to the Norman radii adjusted pore size well known to those skilled in the art. Determination of Norman radii adjusted pore size is described, for example, in Cook, M.; Conner, W. C., "How big are the pores of zeolites?" Proceedings of the International Zeolite Conference, 12th, Baltimore, Jul. 5-10, 1998; (1999), 1, pp 409-414.

One of ordinary skill in the art will understand how to determine the pore size (e.g., minimum pore size, average of minimum pore sizes) in a catalyst. For example, x-ray diffraction (XRD) can be used to determine atomic coordinates. XRD techniques for the determination of pore size are described, for example, in Pecharsky, V. K. et at, "Fundamentals of Powder Diffraction and Structural Characterization of Materials," Springer Science+Business Media, Inc., New York, 2005. Other techniques that may be useful in determining pore sizes (e.g., zeolite pore sizes) include, for example, helium pycnometry or low-pressure argon adsorption techniques. These and other techniques are described in Magee, J. S. et at, "Fluid Catalytic Cracking: Science and Technology," Elsevier Publishing Company, Jul. 1, 1993, pp. 185-195. Pore sizes of mesoporous catalysts may be determined using, for example, nitrogen adsorption techniques, as described in Gregg, S. J. at al, "Adsorption, Surface Area and Porosity," 2nd Ed., Academic Press Inc., New York, 1982 and Rouquerol, F. et al, "Adsorption by powders and porous materials. Principles, Methodology and Applications," Academic Press Inc., New York, 1998.

Regeneration Temperature—The catalyst may be regenerated under flowing air gas at elevated temperatures in order to remove heavier hydrocarbons (coke) from the active catalyst structure. The maximum temperature used in this step is referred to as the "regeneration temperature."

Residence Time (τ)—Residence time is the time a substance is in the reaction vessel. It can be defined as the volume of the catalyst bed divided by the flow rate (by volume per second) of gases into the reactor. τ=volume of Catalyst bed (m$^3$)/volumetric flow of reactants (m$^3$/s).

Selectivity—The term "selectivity" refers to the amount of production of a particular product (or products) as a percent of all products resulting from a reaction. For example, if 100 grams of products are produced in a reaction and 80 grams of olefins are found in these products, the selectivity to olefins amongst all products is $^{80}/_{100}$=80%. Selectivity can be calculated on a mass basis, as in the aforementioned example, or it can be calculated on a molar basis, where the selectivity is calculated by dividing the moles a particular product by the moles of all products. Unless specified otherwise, selectivity is on a mass basis. For propane dehydrogenation, selectivity is the mass of propylene produced divided by the mass of all products.

WHSV—The term WHSV refers to the Weight Hourly Space Velocity and is defined as the weight of reactant fed to a reactor per hour divided by the weight of the catalyst in the reactor Yield—The term "yield" is used herein to refer to the amount of a product flowing out of a reactor divided by the amount of reactant flowing into the reactor, usually expressed as a percentage or fraction. Mass yield is the mass of a particular product divided by the mass of feed used to prepare that product. When unspecified, "%" refers to mass % which is synonymous with weight %. Ideal gas behavior is assumed so that mole % is the same as volume % in the gas phase. For propane dehydrogenation, mass yield is the mass of propylene produced divided by the mass of propane fed. Mass yield of the inventive processes are preferably at least 50% in a single pass, preferably at least 70%.

As is standard patent terminology, the term "comprising" means "including" and does not exclude additional components. Any of the inventive aspects described in conjunction with the term "comprising" also include narrower embodiments in which the term "comprising" is replaced by the narrower terms "consisting essentially of" or "consisting of." As used in this specification, the terms "includes" or "including" should not be read as limiting the invention but, rather, listing exemplary components. As is standard terminology, "systems" include to apparatus and materials (such as reactants and products) and conditions within the apparatus.

EXAMPLES

Example 1

1.2 gm of Zinc Nitrate Hexahydrate, 11 gm of Titanium Oxy-Sulfate and 0.9 gm of Zirconium Tetrachloride inorganic salts were dissolved in 500 ml of deionized water. The salt solution was heated to 55° C. while stirring. When the desired temperature was reached, 2 molar aqueous solution of ammonium hydroxide was added to the inorganic salts solution drop-wise till the mixture reached the pH of 7.3. The resulting precipitate was isolated by filtration and stirred in an aqueous solution of 0.1 M ammonium hydroxide for 30 minutes at room temperature followed by filtration. The precipitate was subsequently isolated by filtration and stirred in an aqueous solution of 0.25 M ammonium nitrate for 30 minutes at room temperature, filtered and dried overnight and then calcined to a temperature of 815° C. for 4 hours to produce the mixed-metal oxide catalyst. This catalyst is designated as Catalyst A.

Example 2

The catalyst was prepared as in Example 1 with the difference being that the amount of Zinc Nitrate Hexahydrate dissolved was 18 gm. This catalyst is designated as Catalyst B

Example 3

The catalyst was prepared as in Example 1 with the difference being that the amount of Zinc Nitrate Hexahydrate dissolved was 27.45 gm. This catalyst is designated as Catalyst C.

Example 4

The catalyst was prepared as in Example 1 with the difference being that the amount of Zinc Nitrate Hexahydrate dissolved was 33.6 gm. This catalyst is designated as Catalyst D.

Example 5

The catalyst was prepared as in Example 1 with the difference being that the amount of Zinc Nitrate Hexahydrate dissolved was 42 gm. This catalyst is designated as Catalyst E.

Example 7

The catalyst was prepared as in Example 2 with the difference being that after the calcination at 815° C., 4 gm of alkaline earth metals modified Dispal binder (T25N4-80) dispersed in 10 gm of deionized water for 30 minutes, was mixed with the mixed-metal oxide catalyst followed by drying and calcining at 650° C. to improve the mechanical strength of the catalyst. This catalyst is designated as Catalyst G.

Example 8

3.7 gm of Zinc Nitrate Hexahydrate, 2 gm of Titanium Oxy-Sulfate and 0.4 gm of Zirconium Tetrachloride inorganic salts were dissolved in 15 ml of deionized water. The salt solution was heated to 55° C. while stirring. When the desired temperature was reached, the solution was added to 18 gm of alumina support (Catalox SBA 150) via incipient wetness impregnation technique followed by drying and calcination at 815° C. to produce mixed-metal oxide catalyst on alumina support. The catalyst was tested for mechanical strength. This catalyst is designated as Catalyst H.

Example 9

6 gm of Zinc Oxide, 6 gm of Titanium Oxide, and 1.4 gm of Zirconium Oxide were slurried in 55 ml of deionized water for 30 minutes followed by drying and calcining at 815° C. to produce mixed-metal oxide catalyst. This catalyst is designated as Catalyst I.

Example 10

6 gm of Zinc Oxide, 6 gm of Titanium Oxide, and 1.4 gm of Zirconium Oxide were slurried in 55 ml of deionized water for 30 minutes. 5.7 gm of alkaline earth metals modified Dispal (T25N4-80) was added to the slurry and mixed for 30 minutes followed by drying and calcining at 815° C. to produce mixed-metal oxide catalyst. This catalyst is designated as Catalyst J.

Example 11

Propane dehydrogenation experiments were performed using a fixed-bed reactor such that the $d_T/d_P>10$ (ratio of diameter of reactor tube to diameter of catalyst particles) and $L/d_P>50$ (ratio of length of catalyst bed to diameter of catalyst particles) to ensure plug-flow behavior. The catalyst of interest was first loaded into a quartz glass lined reactor. The catalyst was activated in dry air at atmospheric pressure at a temperature of 600° C. for 4 hours. Following activation, the reactor was allowed to heat up to reaction temperature of 650° C., then purged with dry nitrogen for 0.5 hours. Propane was fed to the reactor at a WHSV equal to 10 hr$^{-1}$. The flow rate was controlled by a Brooks mass flow controller. Product samples were taken 7 seconds after the start of reaction and were analyzed on GCs having Petrocol DH and Plot Q columns. The catalyst was regenerated at 650° C. by first purging the reactor with nitrogen and then passing air over the catalyst. The results are shown in Table 1.

TABLE 1

Catalytic performance of mixed-metal oxides for propane dehydrogenation

| Catalyst | Zn (wt %) | Activity Parameter | Selectivity Parameter | Stability Parameter |
|---|---|---|---|---|
| A | 4 | 69623 | 0.24 | not measured |
| B | 36 | 98538 | 0.26 | 0 |
| C | 44.8 | 123711 | 0.21 | not measured |
| D | 48 | 98538 | 0.13 | not measured |
| E | 52.8 | 92851 | 0.14 | not measured |
| F | 60 | 64913 | 0.23 | not measured |
| G | 25.2 | 95668 | 0.24 | 0 |
| I | 36 | 20985 | 4 | not measured |
| J | 26.8 | 113772 | 0.19 | 0 |

As shown in the data table, we discovered, surprisingly, that catalysts containing relatively high Zn loading (believed to be at least about 20% or at least about 30% to about 70 mass % Zn) exhibited a substantially superior activity parameter along with high selectivity for olefins.

Example 12

Chemical composition of Catalyst B was measured using Inductively coupled plasma mass spectrometry. The results are shown in Table 2.

TABLE 2

Chemical composition of mixed-metal oxide Sample B.

| Oxide | Weight (%) |
|---|---|
| ZnO | 48.87% |
| TiO$_2$ | 41.58% |
| ZrO$_2$ | 9.35% |
| SO$_3$ | 0.20% |
| Total | 100.00% |

Example 13

Physical properties of Catalyst G were measured to characterize its surface area, bulk density, average particle diameter and attrition strength. The results are shown in Table 2.

TABLE 3

Physical properties of mixed-metal oxide Sample G.

| Parameter | Value | Units |
|---|---|---|
| BET Surface Area | 11 | m$^2$/gm |
| Bulk Density | 810 | kg/m$^3$ |
| Average Particle Diameter | 65 | μm |
| Attrition Index | 1.3 | wt %/hr |

The invention claimed is:

1. A mixed metal oxide catalyst suitable for the dehydrogenation of paraffins having 2-8 carbon atoms, comprising a catalyst composition of the general formula (AC) (CS) (ST) wherein
   a) AC (Active Catalyst) represents oxides of zinc (Zn) wherein the catalyst comprises at least 20 mass % Zn,
   b) CS (Catalyst Support) represents oxides of aluminum (Al), silicon (Si), and titanium (Ti) or mixtures thereof,
   c) ST (Support Stabilizer) represents oxides of metals selected from the group of cerium (Ce), dysprosium (Dy), erbium (Er), europium (Eu), gadolinium (Gd), lanthanum (La), neodymium (Nd), praseodymium (Pr), samarium (Sm), terbium (Tb), ytterbium (Yb), yttrium (Y), tungsten (W), zirconium (Zr), or mixtures thereof, and
   characterizable by a Activity Parameter >90,000, Selectivity Parameter <0.5 and a stability parameter <0.005 using a test where the mixed metal oxide catalyst is loaded in a fixed-bed reactor such that the 50>dT/dP>10 (diameter of tube to diameter of catalyst particles) and 200>L/dP>50 (length of catalyst bed to diameter of catalyst particles) and 2>dP>0.5 mm exposed to a feed stream of propane at a temperature of 650° C., atmospheric pressure and a feed rate of 10 hr-1 weight hourly space velocity.

2. The catalyst composition according to claim 1 wherein the catalyst is characterizable by an activity parameter of between 90,000 and about 125,000 using a test where the mixed metal oxide catalyst is loaded in a fixed-bed reactor such that the 50>dT/dP>10 (diameter of tube to diameter of catalyst particles) and 200>L/dP>50 (length of catalyst bed to diameter of catalyst particles) and 2>dP>0.5 mm exposed to a feed stream of propane at a temperature of 650° C., atmospheric pressure and a feed rate of 10 hr-1 weight hourly space velocity.

3. The catalyst composition according to claim 1 wherein the active catalyst (AC) species (Zn) comprises 30 to 70 or 40 to 60 wt % of the total weight of the catalyst.

4. The catalyst composition according to claim 1 wherein the catalyst support (CS) comprises 20 to 70 or 25 to 70 or 30 to 70 or no more than 60 or no more than 50 wt % of the total weight of the catalyst.

5. The catalyst composition according to claim 1 wherein the support stabilizer (ST) comprises 0.1 to 20 or 0.2 to 15 or 0.3 to 10 wt % of the total weight of the catalyst.

6. The catalyst composition according to claim 1, wherein said catalyst composition has less than 100 ppm by weight of either platinum (Pt) or chromium (Cr).

7. The catalyst composition according to claim 1 wherein the BET surface area is at least 5 m2/g.

8. A method for preparing a catalyst composition as defined in claim 1 comprising the steps of
a) dissolving salts of active material, catalyst support and support stabilizer in a solvent;
b) coprecipitating the salts using a precipitating agent;
c) washing the resultant precipitate with a solvent;
d) drying and calcining the resultant precipitate to produce the mixed metal oxide catalyst.

9. A method for preparing a catalyst composition as defined in claim 1 comprising the steps of:
a) making a slurry comprising oxides of the active catalyst, catalyst support and support stabilizer in water;
b) spray-drying the slurry to produce spherical particles;
c) calcining the spray-dried particles to produce the mixed metal oxide catalyst.

10. A method for preparing a catalyst composition as defined in claim 1 comprising the steps of:
a) making a slurry comprising oxides of the active catalyst, catalyst support, support stabilizer and hydrated alumina in water;
b) modifying the slurry with alkaline earth metal salts
c) drying and calcining the slurry to produce the mixed metal oxide catalyst.

11. A method for preparing a catalyst composition as defined in claim 1 comprising the steps of:
a) providing a salt solution comprising salts of active catalyst, catalyst support, and support stabilizer dissolved in a solvent;
b) impregnating porous spheres with the salt solution;
c) drying and calcining the porous spheres to produce the mixed metal oxide catalyst.

12. The method according to claim 11 wherein porous spheres are selected from the group of alumina, silica, titania, zirconia, kaolin, meta-kaolin, bentonite, attapulgite, or mixtures thereof.

13. The method according to claim 1, wherein the catalyst is calcined at 500-1100° C., preferably at 600-900° C. and most preferably at 700-850° C. for 2-6 hrs in an oxygen containing atmosphere, preferably air.

14. The method according to claim 11 wherein the volume average pore diameter of the porous bead is in the range of 3-3000 nanometers.

15. The catalyst composition according to claim 1 wherein the number average particle diameter of the mixed-metal oxide catalyst is in the range of 30-3000 microns.

16. The catalyst composition according to claim 1 wherein the Air Jet Index is less than 10 and more preferably less than 5.

17. The catalyst composition according to claim 1 wherein the catalyst particles can be characterized as Geldart A or Geldart B powders.

18. A process of dehydrogenating a paraffin (preferably propane or isobutane), comprising contacting the paraffin with the catalyst of claim 1 in a reaction chamber under conditions sufficient to dehydrogenate the paraffin and resulting in an olefin.

19. A method for preparing a mixed metal oxide dehydrogenation catalyst composition, comprising the steps of:
a) dissolving salts of Zn, catalyst support and support stabilizer in a solvent to form a solution wherein the mass ratio of Zn to all dissolved metals is in the range of 0.2 to 0.7, preferably 0.3 to 0.6; optionally filtering the solution;
wherein the salts of catalyst support comprise salts of Al, Si, and/or Ti and wherein the salts of support stabilizer comprise salts of cerium (Ce), dysprosium (Dy), erbium (Er), europium (Eu), gadolinium (Gd), lanthanum (La), neodymium (Nd), praseodymium (Pr), samarium (Sm), terbium (Tb), ytterbium (Yb), yttrium (Y), tungsten (W), zirconium (Zr), or mixtures thereof;
b) coprecipitating the salts using a precipitating agent to form a precipitate;
c) washing the precipitate with a solvent; and
d) drying and calcining the resultant precipitate to produce the mixed metal oxide catalyst.

20. The method of claim 19 wherein the ratio mass Zn/[mass Al+Si+Ti+Ce+Dy+Er+Eu+Gd+La+Nd+Pr+Sm+Tb+Yb+Y+W+Zr+Zn], is in the range of 0.20 to 0.70.

21. The method of claim 18 wherein the precipitating agent comprises aqueous ammonia.

* * * * *